United States Patent [19]

Mohr et al.

[11] Patent Number: 4,767,599

[45] Date of Patent: Aug. 30, 1988

[54] SILICATE-CONTAINING ANTIFREEZE WITH CARBOXY-SUBSTITUTED ORGANOSILICON STABILIZER

[75] Inventors: Paul H. Mohr, Chappaqua; Enrico J. Pepe, Amawalk, both of N.Y.

[73] Assignee: First Brands Corporation, Danbury, Conn.

[21] Appl. No.: 109,575

[22] Filed: Oct. 16, 1987

Related U.S. Application Data

[63] Continuation of Ser. No. 855,380, Apr. 24, 1986, Pat. No. 4,701,277, which is a continuation-in-part of Ser. No. 781,985, Sep. 30, 1985, abandoned.

[51] Int. Cl.$^4$ .............................................. C23F 14/02
[52] U.S. Cl. ...................................... 422/13; 252/75; 252/78.3; 422/7
[58] Field of Search .................. 422/7, 13, 14; 252/75, 252/78.3

[56] References Cited

U.S. PATENT DOCUMENTS 3,198,820  8/1965  Pines et al. ........................... 556/437
3,337,496  8/1967  Pines et al. ........................... 528/39
3,793,360  2/1974  Prokai et al. ........................ 556/437

Primary Examiner—Robert Wax
Attorney, Agent, or Firm—Gary L. Wamer

[57] ABSTRACT

A silicone/silicate-containing antifreeze characterized by dilute aqueous stability includes substituted organosilicon carboxylates characterized by the following formula:

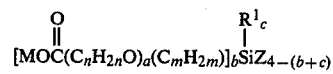

wherein M is a monovalent cation such as, for example, sodium; Z represents a moiety hydrolyzable to silanol; $R^1$ represents hydrogen, a monovalent hydrocarbon radical such as methyl, ethyl, phenyl, and the like or a substituted monovalent hydrocarbon radical; a has a value from 0 to 20, b has a value of 1 or 2, c has a value of 0 or 1, n has a value of 2, 3, or 4, and m has a value of from 3 to 15 when a is other than 0 and from about 7 to about 15 when a is 0.

43 Claims, No Drawings

SILICATE-CONTAINING ANTIFREEZE WITH CARBOXY-SUBSTITUTED ORGANOSILICON STABILIZER

CROSS-REFERENCE TO RELATED APPLICATION

The subject matter of the present invention is related to the subject matter of commonly-assigned, co-pending U.S. application Ser. No. 752,561, filed on July 10, 1985, now U.S. Pat. No. 4,676,919, which is a continuation-in-part of U.S. application Ser. No. 633,208, filed on July 23, 1984, now abandoned.

FIELD OF THE INVENTION

The present invention relates generally to an antifreeze concentrate and, more specifically, to an antifreeze composition containing silicate stabilized by selected carboxy-substituted organosilicon compounds.

BACKROUND OF THE INVENTION

Corrosion-inhibitive heat transfer compositions of aqueous alcohol solutions heretofore have been widely employed in heat exchange systems associated with internal combustion engines, solar systems, and the like, to depress the freezing point of the coolant, to raise its boiling point, and provide corrosion inhibition. Since conventional alcohol-based heat transfer fluids, such as automobile antifreezes, have the tendency to corrode the metal (e.g., aluminum, copper, iron; brass and solder) surfaces of the heat transfer system, these fluids generally contain corrosion inhibitors to minimize this phenomenon.

Two U.S. patents are particularly noteworthy, as these are considered to be representative of the start-of-the-art antifreeze technology. U.S. Pat. Nos. 3,341,469 and 3,337,496 thus disclose an aqueous alcohol composition employing organosiloxane/silicate copolymers wherein the siloxane can contain polyethyleneoxy organosilicon species. As an additional illustration, U.S. Pat. No. 3,198,820 discloses an aqueous alcohol antifreeze containing a carboxyl organosiloxane/silicate copolymer.

Corrosion-inhibitive heat transfer compositions of the type described in the '469 and '496 patents have enjoyed wide usage. A composition of this type typically has superior shelf-life, does not attack rubber parts in cooling systems, is characterized by low levels of foam formation, and is useful over a wide temperature range even after prolonged periods in service.

In addition to providing corrosion protection for cooling system metals, the art has recognized the need to provide an antifreeze which does not gel in concentrate form. Thus, U.S. Pat. No. 4,149,985 teaches that the pH at the time of silicate addition to such antifreeze concentrates must be between 9.5 and 10.5 (providing a final concentrate pH of about 11) in order to minimize concentrate silicate stability problems during storage. Unfortunately, these antifreeze concentrates are subject to annoying gelation problems from time to time, although these antifreezes afford reasonable latitude in preparation and use.

Many prior patents in this field, e.g., the '469, '496, '985 and '820 patents identified herein, suggest that an extremely large number of silanes are useful to form stable polymers with inorganic silicates which, in ethylene glycol concentrates, are not subject to gelation and the manufacturing and dispensing problems associated with gel formation. These prior patents likewise suggest that the pH range may vary widely, typical ranges disclosed being from 7.0 up to 12.0 or so.

Prior work in this field also suggests that relatively large amounts of silicates (as much as 5,000 ppm of Si), can be appropriately stabilized. However, it has been found that these prior art suggestions are not particularly useful in predicting suitability of silanes for stabilizing silicate in aqueous antifreezes.

Pursuant to the invention disclosed in commonly-assigned U.S. application Ser. No. 752,561, it has been found that relatively low pH antifreezes of less than about 10, having concentrate pHs of between about 5.8 and about 7.5, impart highly effective protection against aluminum corrosion in comparison to state-of-the-art antifreezes and are silicate gel resistant in the concentrate when using selected silanes.

Still other prior work in this field is reflected in British Patent No. 2,018,266A and U.S. Pat. Nos. 4,333,843, and 4,386,154. In general, this prior work suggests the use of a wide variety of siliconate/phosphonate compounds as stabilizers against gel formation of silicates in an antifreeze. The use of the alkali metal and tetraalkyl ammonium derivatives are also disclosed.

In addition to the foregoing, the prior art is replete with attempts to provide antifreeze formulations which are gel resistant and impart the desired protection for engine cooling systems. The essentially uniform focus, applicants believe, has been on the ability of the antifreeze formulation in the concentrate to avoid undue gelling. Yet, it is state-of-the-art practice for antifreeze manufacturers to recommend that antifreeze concentrates be diluted with water to provide a 50 volume percent working antifreeze (viz.—the antifreeze concentrate being diluted with an equal volume of water).

It has now been found that many silicone stabilizers that are satisfactory in providing stability in an antifreeze concentrate appear to destabilize the silicate in the water-diluted or working antifreeze, causing a portion of the silicate corrosion inhibitor to form an insoluble species in solution. At the very least, this will result in a loss of corrosion inhibition efficiency which could well be substantial. This is considered to be a rather surprising discovery in light of the extensive prior efforts in this field.

This destabilization, upon dilution to provide a working antifreeze, thus presents a serious obstacle which must be overcome. Stability of the antifreeze composition in concentrate form provides no assurance that the concentrate, upon dilution with water to yield the working antifreeze, will retain the desired corrosion protection intended with a silicate antifreeze formulation. In addition to the potential loss of corrosion protection, destabilization may well result in silicate precipitation, causing blockage of the radiator tubes in an automobile cooling system.

It has also been found that many silanes are aggressive towards at least aluminum surfaces, viz.—such silanes tend to promote aluminum corrosion. Accordingly, to provide an antifreeze useful in systems having aluminum surfaces, it will be highly desirable to utilize silanes that are at least relatively passive towards aluminum.

Still further, it would be highly desirable to provide an antifreeze that is capable of retaining adequate stability, yet which allows greater latitude in formulation. For example, an antifreeze with a higher RA (i.e.—reserve alkalinity) is often desirable. This also allows maintenance of the desired working pH for a longer period of time. Yet, such a high RA composition generally tends to lessen the desired stability. Similarly, it is often desirable to incorporate supplemental corrosion inhibitors, many of which are ionic in nature, yet the presence of ionic supplemental corrosion inhibitors likewise tends to exacerbate the silicate stability problem.

The synthesis of certain alkoxy derivatives is likewise disclosed in the literature. Thus, in the *Journal of American Oil Chemist's Society*, Vol. 51, pages 363-367, August, 1974, the synthesis of

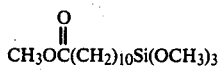

is disclosed. The synthesis of the corresponding ethoxy compound is disclosed in *Chem. Abstracts*, Vol. 67, 64522n, 1967. No utility as a stabilizer is disclosed.

OBJECTS OF THE INVENTION

It is a principal object of the present invention to provide a silicate-containing antifreeze that is stable in concentrate form, yet, upon dilution with water, is characterized by exceptional silicate stability in the diluted antifreeze composition.

Yet another and related object of this invention is to provide an antifreeze which, upon dilution with water, provides highly effective and efficient protection for internal combustion engine cooling systems.

A still further object of the present invention is to provide a stable antifreeze concentrate which maintains its stability when diluted with water.

Another object of this invention provides an antifreeze which retains the desired stability while allowing substantial latitude in formulation.

These and other objects will become apparent in view of the following detailed description.

SUMMARY OF THE INVENTION

In general, the present invention relates to an antifreeze composition comprising: (a) an alcohol, (b) a buffer in an amount sufficient to maintain a pH in the desired range for the working antifreeze, (c) a silicate in a corrosion-inhibiting effective amount, and (d) an organosilicon compound present in an amount effective to stabilize the silicate component. Pursuant to the present invention, it has been discovered that enhanced stability for the silicate in the working antifreeze can be imparted by inclusion of, as component (d), certain substituted organosilicon carboxylates. More specifically, the substituted organosilicon carboxylates may be characterized by the following formula:

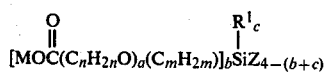

wherein M is a monovalent cation as will be detailed herein; Z represents a moiety hydrolyzable to silanol; $R^1$ represents hydrogen, a monovalent hydrocarbon radical such as methyl, ethyl, phenyl, and the like or a substituted monovalent hydrocarbon radical; a has a value from 0 to 20, b has a value of 1 or 2, c has a value of 0 or 1, n has a value of 2, 3, or 4, and m has a value of from about 3 to about 15 when a is other than 0 and from about 7 to about 15 when a is 0.

The resulting antifreeze composition is readily soluble in water to provide a working antifreeze. Moreover, upon dilution to provide the working antifreeze, the resulting composition should provide enhanced and efficient corrosion protection in an engine cooling system inasmuch as the amount of silicate available to provide such corrosion protection can be optimized.

The more specific aspects of the present invention and the particularly preferred embodiments will be described in the detailed description.

DETAILED DESCRIPTION OF THE INVENTION

Alcohol Component

The alcohol component may be any of the many useful species known in the art for formulating antifreeze concentrates. Representative useful alcohols include methanol, ethanol, propanol, butanol, ethylene glycol, diethylene glycol, propylene glycol, dipropylene glycol, glycerol, butylene glycol, the monoethylether of glycerol, the dimethyl ether of glycerol, alkoxy alkanols (such as methoxyethanol), and mixtures thereof. The preferred alcohol is selected from the group consisting of ethylene glycol, diethylene glycol, propylene glycol, dipropylene glycol and mixtures thereof.

Buffer

As was the case with the alcohol component, useful buffers may be any of the many that are known and have been described in the antifreeze concentrate field. The particular buffer or mixtures of buffers used, as is known, will depend upon the pH desired for the working antifreeze which, in turn, may be influenced by the particular metals used in the engine cooling system.

When measured on a 50:50 volume/volume of antifreeze concentrate and water (the general composition recommended for a working antifreeze), the pH will generally be maintained between a level of about 8 and about 11. Below a pH of about 8, the antifreeze would generally be expected to be unduly corrosive to ferrous metals. On the other hand, utilizing a working pH of more than about 11 would be expected to promote relatively high levels of aluminum corrosion and aluminum transport deposits.

In accordance with the present invention, it is preferred, when utilizing the 50:50 volume to volume mixture, to employ a pH within the range of from about 9 to about 11, more preferably between about 9 and about 10.5. However, when optimizing the system to favor minimized corrosiveness toward amphoteric metals and to minimize aluminum transport deposition in a cooling system including such metals, a pH within the range of from about 8 to about 10.5 will be preferred.

Representative examples of suitable buffers include ammonium, alkanolamine and alkali metal borates, tetraalkyl and tetraaryl-ammonium borates and borate mixtures thereof; alkali metal phosphates; ammonium phosphates, alkanolamine phosphates, and tetraalkyl- and tetraaryl-ammonium phosphates, and phosphate mixtures thereof; alkali metal, ammonium, and amine, benzoates and substituted benzoates; salts of the dibasic acids, such as sebacic and azelaic acids, having 6 to 20 carbons, and mixtures thereof; and mixtures of any of the above buffers; said buffer generally being present in an amount of between 1 and about 5 wt. percent, based on the weight of the concentrate.

Among the useful buffers identified, a borate or a mixture of borates is the preferred buffer and may be conveniently added as the alkali metal salt. After adding the salt, addition of sodium hydroxide or a mixture of boric acid and sodium hydroxide can be used to provide the desired metaborates and/or tetraborates in the concentrate.

The buffer provides the desired use or working pH and capacity for maintaining this pH during extended use of the antifreeze when the pH would otherwise change due to changes in the compositions of the antifreeze over time. These functions are also achieved using soluble phosphate salts of non-alkali metals such as ammonium phosphate and alkanolamine phosphate and the other organic acid derivatives mentioned above. However, these amine phosphates are less preferred than the alkali metal borates since the former tend to promote the corrosion of cuprous metals.

Silicate Component

Any silicate known for use in antifreeze concentrates may be employed as the silicate component. A variety of useful inorganic and organic silicates are thus known.

Useful inorganic silicates are represented by units having the empirical formula:

$$(MO)_w\text{Si}\underset{|}{-}O_{\frac{4-p}{2}}$$
$$(OH)_v$$

where M is a monovalent cation that forms a glycol soluble silicate selected from the group consisting of sodium, potassium, lithium, rubidium and tetraorganoammonium cations, $\underline{w}$ has a value of from 1 to 4 inclusive, $\underline{v}$ has a value from 0 to 3 inclusive and p has a value from 1 to 4 inclusive which is equal to the sum of $\underline{w}$ and $\underline{v}$.

Useful organic silicates are the esters encompassed by the formula:

$$\text{Si(OR)}_4$$

wherein R is selected from the group consisting of alkyl, aryl, alkoxyalkyl, alkoxyaryl, hydroxyalkoxy, and mixtures thereof. In use, when diluted with water, it is believed that such esters in a relatively low pH range will form smaller silicate aggregates, which in turn have a greater proficiency in inhibition of metal corrosion as compared to the inorganic silicates.

Further, with respect to such organic silicates, as is known, any R group selected should not sterically hinder the silicate such that hydrolysis to the silanol cannot be effected. Similarly, an R group should not be employed which will cause the silicate to be insoluble in the alcohol used for the antifreeze.

As illustrative examples of useful inorganic silicates, potassium and sodium silicates are appropriate. Useful organic silicate esters include: alkyl silicates such as methyl silicate, ethyl silicate, butyl silicate and amylsilicates; aryl silicates such as benzyl and tolyl silicates; mixed alkyl silicates such as methyl ethyl silicate; mixed aryl silicates such as benzyl tolyl silicate; mixed alkyl aryl silicates such as methyl benzyl silicate and ethyl tolyl silicate; glycol silicates such as hydroxyethyl silicate and hydroxypropyl silicate; and polyhydroxy alkyl silicates such as glycerol silicate and pentaaerythritol silicate; oxyalkylene silicates such as methoxy diethylene glycol silicate, i.e. METHYL CARBITOL ® silicate; and mixtures of the above. The preferred organic silicate is tetra-hydroxyethyl orthosilicate. Also useful within the scope of the present invention is the well-known class of partially condensed orthosilicate esters.

The amount of silicate in the concentrates used to make the antifreezes of this invention can vary over a wide range, but is preferably present in an amount of between 40 and 1000 ppm of equivalent Si, preferably at least about 100 ppm, and more preferably in an amount between 300 and 700 ppm. Below 40 ppm, insufficient silicate would generally be provided to minimize metal corrosion in the automobile cooling system, whereas above 1000 ppm, silicate gels may be encountered in the antifreeze concentrate and in the working antifreeze.

It should be appreciated that the level of silicate employed will depend somewhat upon the operating pH range. Thus, the maximum silicate level for the lower pH ranges will preferably be no more than about 700 ppm of equivalent Si to minimize undesirable silicate gels.

Substituted Organosilicon Carboxylate

As previously discussed, and pursuant to a principal aspect of the present invention, this component may be characterized by the following formula:

$$[\underset{\|}{\overset{O}{M O C}}(C_nH_{2n}O)_a(C_mH_{2m})]_b\text{Si}\underset{|}{\overset{R^{1c}}{}}Z_{4-(b+c)}$$

the various constituents and values being as previously described.

More particularly, with respect to the monovalent cation, M, any of a variety of cations may be utilized. The principal functional requirements are that solubility be provided and that the constitutent selected be, of course, ionizable. Illustrative useful examples include sodium, potassium, lithium, rubidium, and tetraorganoammonium cations such as tetramethyl ammonium and the like, with sodium and potassium being preferred.

As to the $R^1$ constituent, any of a wide variety of monovalent hydrocarbon groups may be utilized. The principal functional requirement is that the group selected should not render either the silane or the silicone/silicate copolymer insoluble. Accordingly, relatively large alkyl chains and the like should be avoided.

The hydrolyzable moiety Z can include any hydrolyzable moiety attached to silicon, such as, for example, halogens, such as F, Cl, Br, and I; hydrogen; hydrocarbonoxy, such as —OCH$_3$, —OCH$_2$CH$_3$, —OCH$_2$C-H$_2$OH, —OCH$_2$CH$_2$O—, —O(CH$_2$CH$_2$O)$_2$H, —O(CH$_2$CH$_2$O)$_7$CH$_3$ $$-\underset{\|}{\overset{O}{O C}}(CH_2)_{10}O\text{Si}\underset{|}{\overset{R^{1c}}{}}Z_{4-(b+c)},\ -\underset{\|}{\overset{O}{O C}}(CH_2)_7CH=CHCH_3,$$

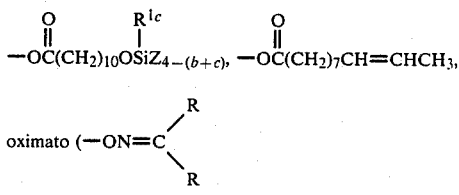

in which R is a monovalent hydrocarbon radical such as methyl or ethyl), organoamino

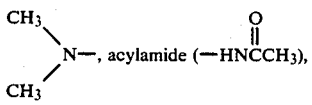

and haloalkoxy, such as,

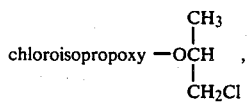

hydroxyl (—OH), and

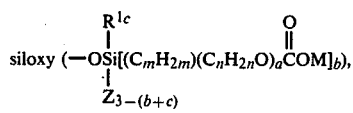

the various constituents and values being as described in the general formula for the organosilicon carboxylates. The broad useful class of moiety Z would include, for example, acyloxy containing species, alkyloxy containing species, aryloxy containing species, aralkyloxy containing species, alkaryloxy containing species, alkyleneoxy containing species, hydroxy alkyloxy containing species, hydroxy polyalkyleneoxy alkyloxy containing species, alkoxy polyalkyleneoxy alkyloxy containing species, acyloxy polyalkyleneoxy alkyloxy containing species, alkoxy alkyloxy containing species, acyloxy alkyloxy containing species, cyano alkyloxy containing species, cyano polyalkyleneoxy alkyloxy containing species, amino alkyloxy containing species, dialkylamino alkyloxy containing species, alkanolamino alkyloxy containing species, dialkanolamino alkyloxy containing species, carboxy alkyloxy containing species, carboxy polyalkyleneoxy alkyloxy containing species, carboalkoxy containing species and carboalkoxy alkyloxy containing species.

Thus, there is substantial breadth in selecting the hydrolyzable group, Z. The principal requirement is that the particular group selected not prevent the silane from being soluble in the alcohol employed.

The synthesis of these carboxylates may be carried out by using known techniques. For example, a conventional hydrosilation of the particular olefinically-terminated intermediate

is first carried out using a platinum catalyst and chlorosilane. The resulting trichlorosilane intermediate adduct can then be esterified as is known. Continuous removal of by-product HCl can then be effected during the esterification process. Reaction with a base, for example, sodium hydroxide or potassium hydroxide or sodium methoxide in methanol, is then employed to form the desired metal carboxylate. The amount of base used will be determined by the level of the metal alkyl carboxylate desired in the final product. The amount of base used can range from the amount needed to neutralize any residual Si-Cl to that necessary to convert the alkyl carboxylate to the metal carboxylate. An excess of base over that necessary to convert to the metal carboxylate may be used as well.

The synthesis of the carboxylates which include alkyleneoxy moieties can be carried out using known techniques. For example, there is first carried out a base-catalyzed polymerization of the alkylene oxide or oxides using an initiator or starter such as allyl alcohol. Following capping with an acrylate (e.g. ethyl acrylate), a conventional hydrosilation is effected. Further processing is then carried out as has been described herein.

Useful substituted organosilicon carboxylates may be derived by utilizing precursors of the following formula which are hydrolyzable or saponifiable to provide the desired carboxylates:

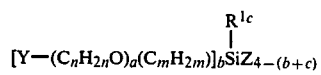

The constituents and values are the same as those described in conjunction with the organosilicon carboxylates utilized in the present invention. As illustrative examples, useful moieties for Y include:

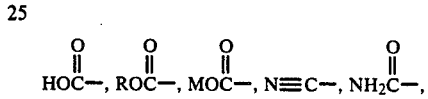

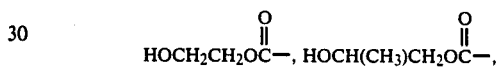

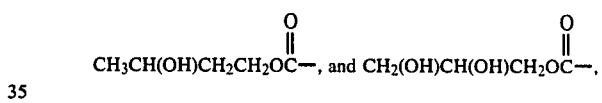

M being an alkali metal and R being a monovalent hydrocarbon radical. Other similar groups that are hydrolyzable or sufficiently saponifiable to carboxylate salt groups may also be employed.

With respect to most of the precursors, the alkoxy intermediate may be converted by a conventional ester exchange. Concerning the cyano and amido precursors, cyanoolefin compounds are available. These compounds may then be converted using hydrosilation, as has been described. The amido precursor may then be obtained by hydrolyzing the cyano precursor.

As will be appreciated, the end of the substituted organosilicon carboxylate molecule that is hydrolyzable to a silanol serves to react with the silicate or silicates employed to form, as generally termed in the art, a copolymer. Accordingly, it is particularly preferred to utilize carboxylates or precursors thereof that will result in silane triols upon hydrolysis. In other words, in the structural formulas provided herein, it is particularly preferred to utilize carboxylates in which c is 0.

Moreover, the active species for corrosion protection is considered to be monomeric silicate. It is accordingly believed that superior performance results and optimized efficiency may be provided by utilizing a system in which there is less opportunity for undesired and inactive silicate polymers to be formed.

Achieving this objective requires employing a silane capable of efficiently stabilizing the silicate species that generate silicate monomer. One aspect of this is to use a silane starting material which is predominantly and preferably all monomeric in form, or if in polymeric or oligomeric form, is capable of relatively rapidly reversing to monomeric silane triol species upon addition to base and alcohol in preparing the antifreeze concentrate. Stated another way, the formation of irreversible silane polymer reduces the stabilizing efficiency of the silane by reducing the number of molecules available for reaction with silicate and can lead to the formation of undesirable precipitates.

Another aspect is to preferably utilize a silane starting material that is soluble in the antifreeze concentrate (viz.—the concentrate appears clear to the naked eye). In this preferred embodiment, it is envisioned that the soluble silane rapidly disperses into the alcohol component so as to avoid any localized, relatively high concentration of silane that could result in undesirable polymerization more readily taking place. Accordingly, when a precursor to a carboxylate is used, it is necessary that the Y moiety employed, if not providing solubility for the silane in the concentrate, be capable of being readily dispersed therein and readily hydrolyzed or saponified to a carboxylate so that solubility results.

Pursuant to a most preferred embodiment of the present invention, the substituted organosilicon carboxylate component is utilized in its glycolized form. It has been found that using the glycolized form provides optimum performance. As an illustrative example, to obtain the glycolized form, a routine hydrosilation is first carried out using a plantinum catalyst and chlorosilane:

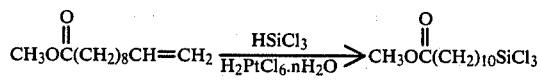

The glycolized form is then obtained by reaction with an excess of ethylene glycol (or any of the other alcohols described herein) to ideally give:

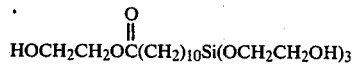

The glycolized reaction product will generally contain a minor amount of residual Si-Cl, and it will be desirable to neutralize the reaction product with base. Since the presence of water will promote some silane polymerization, it will be more desirable to employ an anhydrous base such as solid sodium methoxide in methanol, although KOH or the like may also be used. The amount of base used can range from the amount needed for neutralization to that which will convert the glycolized carboxylate end of the molecule to the metal carboxylate (or an excess).

The principal species resulting (the relative amounts depending upon the extent of neutralization) will be:

 and

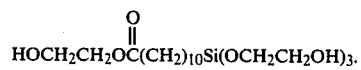

Upon addition to base and alcohol to form the antifreeze concentrate, the aforementioned precursors will be converted to what is considered to be the active species, viz.:

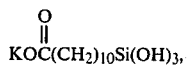

with varying amounts of precursor reaction products generally being present. Complete conversion to the active species can be achieved through full saponification during synthesis. It should be appreciated that this is an idealized structure and that some amount of silane polymer will be present. The amount may be determined by using $^{29}$Si nuclear magnetic resonance.

Any alternative procedure may be utilized to yield the glycolized form. A number of procedures are thus known.

It is believed that the use of the glycolized form will result in optimized performance. The extent of silane polymer formed can thus be minimized; and the propensity for forming undesirable precipitates (due either to an insoluble silane polymer or an insoluble polymer upon reaction of a silane polymer with silicate) will be substantially lessened.

Still further, and while not wishing to be bound to any particular theory, it is believed that the more useful substituted organosilicon carboxylates employed in the antifreeze compositions of the present invention are characterized by an appropriate glycophilic (hydrophilic)/glycophobic (hydrophobic) balance as well as having a satisfactory molecular weight. Without the appropriate molecular weight and balance, it is believed that the organosilicon component tends to destabilize the silicate in the working antifreeze.

This destabilization can manifest itself in the formation of gels within an automobile cooling system. These gels can, in turn, cause blockage of the cooling system radiator tubes as well as, and importantly, result in the aggregation of silicates which render these silicates ineffective as metal corrosion inhibitors.

It is envisioned that the balance described above is necessary to provide what can be termed an adequate driving force which, in effect, increases the likelihood that the organosilicon carboxylate will reach the silicate to then provide the desired copolymer. The result will be what may be viewed as a negatively charged silicate particle (the silicate being considered to be microcolloidal in form), which particles are thus stabilized in the antifreeze.

With regard to the molecular weight considerations, too low a molecular weight silane molecule is believed to possess a greater propensity to homopolymerize, thus depleting the stabilizer, which could result in losing control over the silicate chemistry involved. More particularly, in the absence of adequate stabilization, silicate particles grow excessively to an undesirable size. The function of stabilization is to at least minimize, and preferably eliminate, this excessive silicate particle growth as this ultimately depletes the amount of the active monomeric silicate species available in the working antifreeze. On the other hand, too high a molecular weight will provide a molecule with what may be termed undue bulk. This will tend to interfere with the kinetic equilibrium or actually produce insoluble nonequilibrium products so as to unsatisfactorily reduce the necessary solubility. In general, it has been found that the appropriate balance to provide the desired driving force is fortuitous in that achieving this appropriate balance likewise results in appropriate molecular weight for both the silane stabilizer and the resulting silicone/silicate copolymer.

Stated another way, unduly short chain length carboxylate silicones can be expected to produce high molecular weight homopolymers. In contrast, longer chain length silicone carboxylates have an inherent bulkiness that limits the degree of homopolymerization. However, with silicone carboxylates of undue chain length, where homopolymerization is minimal, undesirable silicate copolymer precipitation in the working antifreeze becomes a major concern.

A determination that the appropriate balance and polymer molecular weight have been provided may be determined in a straightforward manner. Specifically, the "boiling beaker" test (described hereinafter) may be utilized to determine the weight of the precipitate in that test. It is, of course, most preferred that essentially no precipitate be formed in the boiling beaker test. Performance of that level should provide a highly stable antifreeze. Indeed, use of the most preferred embodiment of the present invention should result in less than about 10 mg. precipitate being formed. Also, use of the antifreeze compositions of the present invention will provide improvements in this regard in relation to antifreeze compositions using other silanes. Accordingly, use of this invention should result in precipitates of 60 mg. or less.

In accordance with a preferred aspect of the present invention, organosilicon carboxylates are employed in which, according to the formula previously set forth herein, a is 0, b is 1, c is 0, m is from about 7 to 15, and M is potassium or sodium. Most preferably, m is 10, a, b, c, and M being as described in the preferred embodiment. Other useful carboxylates may be provided according to the formula wherein a is from about 5 to 13 (more preferably about 5 to about 9), b is 1, c is 0, n is 2, and m is 3.

From the standpoint of known synthetic techniques, when a is other than 0 in the formula, m will be either 3 or 4. Accordingly, and conceptually, to provide the optimum glycophilic (hydrophilic)/glycophobic (hydrophobic) balance, the alkyleneoxy component, viz.—$(C_nH_{2n}O)_a$, with, for example, a $(CH_2)_3$ group resulting from the synthesis, should be made equivalent from the balance standpoint to the compound having an additional $CH_2$ chain length of 7. Similarly, as is known, the alkyleneoxy chain character becomes more hydrophobic with the larger alkyleneoxy groups. More specifically, a propyleneoxy group is relatively more hydrophobic than an ethyleneoxy group.

Moreover, in the general sense, when a is other than 0 and one or more alkyleneoxy groups are thus present, suitable compounds are provided by attaining the same glycophilic (hydrophilic)/glycophobic (hydrophobic) balance as is provided when a is 0, viz.—attaining the same balance as with a methylene chain of from about 7 to about 15. More particularly, it is believed that the balance characteristics of a propyleneoxy moiety are essentially the same as that of a methylene moiety. Accordingly, when a methylene chain of 3 from the synthesis results, a propyleneoxy chain of from about 4 to 12 should provide useful materials.

In an all-ethyleneoxy system, having a methylene chain of 3 from the synthesis, an ethyleneoxy chain with an average of 7.5 has slightly more than an optimum level of hydrophilicity. An ethyleneoxy chain of about 5 should provide an optimum balance. Also, and in general, it will be desirable to employ about two ethyleneoxy groups in comparison to one methylene group (in an all methylene system) to provide a molecule having the desired balance. This same general relationship holds true in an ethyleneoxy - propyleneoxy system.

An all-butyleneoxy system will tend to be somewhat more hydrophobic than is the case with a molecule having only methylene groups. In this system, as well as in other alkyleneoxy systems, the appropriateness of the balance in a specific case can be readily determined by straightforward experimentation, viz.—by synthesizing the compound and testing in the boiling beaker test.

The foregoing description proceeds on the basis that an essentially straight chain aliphatic compound is employed. It should be appreciated, however, that if desired, a branched chain compound could be used as could the introduction of aryl groups. The suitability of such substituted compounds can be determined by using the boiling beaker test as described herein.

It should also be apparent that substituted organosilicon compounds other than carboxylates may be used, employing the molecular weight and balance considerations as taught herein. Thus, the teaching of the present invention may be utilized with substituted organosilicon sulfonates, phosphonates, sulfates, and the like. The preparation of materials of these types will of course require alternative synthetic techniques.

It should be appreciated that the silane carboxylates of this invention are most preferably synthesized in such a fashion as to maximize the level of the silane monomer and minimize the amount of the silane oligomers that can be formed. More particularly, two silane monomers can react to form an oligomer having an Si—O—Si bond; and three and more silane molecules can react to form higher oligomers. It is the higher oligomers that are to be avoided, as it is believed that the silane dimer will ultimately, at least in large part, revert to monomer upon addition to alcohol. Maximization of the silane monomer can be achieved by avoiding the presence of water in the synthesis.

The carboxylates can be desirably placed in an excess of an alcohol, such as ethylene glycol, to further minimize the formation of undesirable oligomers prior to use in making the antifreeze. Accordingly, a desirable product comprises the glycolized form described herein, having added thereto base in an amount from that needed to neutralize any residual Si-Cl from the synthesis to that adequate to convert the carboxylate to the metal carboxylate. The amount of the glycolized form in the alcohol can range from as little as about 20 weight percent or less up to 75 weight percent or so, as is desired, with active species levels of about 50 to 75 weight percent being more desirable.

The total silicone portion (i.e., component (d)) of the silicone/silicate polymer, used, of course, in an amount effective to stabilize the level of silicate being employed, is preferably employed in an amount equivalent to between about 10 and 100 ppm of silicon equivalents, based on the weight of the antifreeze concentrate, more preferably between about 25 and about 100 ppm. In general, it will be desirable to employ the silane in an amount about 10 percent (by weight) of that of the silicate. However, the amount may be varied as desired, consistent with the desired economics and performance requirements.

The silicone/silicate polymers formed by mixing the silanes and silicates useful in the composition of this invention are preferably employed in an amount of from about 0.01% to about 10% by weight, based upon the weight of the concentrate, more preferably from about 0.05 weight percent to about 5 weight percent, most preferably from about 0.05 weight percent to about 3 weight percent, based on the weight of the concentrate. Below about 0.01 wt. %, the amount of silicone/silicate is expected to be insufficient to be functionally protective to metals, whereas above about 10 wt. % the cost of the silicone/silicate becomes excessive.

The polymers useful in the present invention can be preformed prior to formulation of the antifreeze or they can be formed in situ in the antifreeze formulation by mixing organosilanes with silicates in the presence of the alcohol being employed. Suitable processes are well-known in the art and are disclosed, for example, in U.S. Pat. Nos. 3,337,496 and 3,312,622, both incorporated herein by reference.

Antifreeze Concentrate and Working Antifreeze

The antifreeze concentrates may contain a limited amount of water, e.g., about 0.1 to about 10 percent by weight of water, based upon the weight of the concentrate. The water present may be inherent in the commercial grade alcohol often used in the preparation of an antifreeze concentrate.

A working antifreeze, as referred to herein, will usually contain at least about 20 volume percent water, based upon the total weight of the antifreeze. In general, to provide the working antifreeze, the antifreeze concentrate is diluted by addition of from about 25 to about 90 percent by weight of water, based upon the weight of the concentrate, to form the corrosion-inhibitive heat transfer composition suitable for introduction into internal combustion engine cooling systems.

Alternatively, if desired, the concentrate (which may be anhydrous) can be utilized as the functional fluid or working antifreeze. More particularly, while it is the current practice to dilute an antifreeze concentrate with water to form the working antifreeze, this is not considered essential.

Still further, it should be appreciated that it is within the scope of the present invention to, in effect, form the antifreeze composition in situ by adding one or more of the components directly into the engine cooling system rather then initially forming a concentrate. Indeed, while not preferred, some utility may be imparted by adding a useful organosilicon carboxylate or its precursor into a cooling system already containing the other components.

Optional Components

The antifreeze compositions of the present invention may be employed for internal combustion engine cooling systems for any of the metals typically used or contemplated. At present, many cooling systems are what may be termed "hybrid" systems, having, in addition to ferrous surfaces,, other metal surfaces such as aluminum or the like. The antifreeze compositions of this invention may be utilized in such hybrid systems as well as, of course, in an essentially ferrous system.

In hybrid and largely ferrous systems, less than optimum corrosion resistance for iron and other non-aluminum metal surfaces is occasionally encountered in the practice of the present invention as is likewise the case with state-of-the-art antifreeze compositions. It is accordingly preferred to utilize in such systems supplementary corrosion inhibitors for the particular metal surfaces involved. A wide variety of such additives are known and may be employed.

Moreover, irrespective of the type of metal surfaces in the particular cooling system, such supplementary inhibitors and other optional additives may desirably be included. In any case, these should be employed in a minor amount, up to about 50 weight percent of the antifreeze concentrate, preferably less than about 10 weight percent.

Typical optional additives include, for example, known corrosion inhibitors for metals such as, for example, molybdates, tungstates, selenates, chromates, borates, organophosphates, carbonates and bicarbonates, sebacates and other dicarboxylic acids, benzoates, hydroxy benzoates or acids thereof, acrylic acid polymers and graft copolymers thereof, silicones, alkali metal nitrates, alkali metal nitrites, tolyltriazole (hereinafter "TTZ"), mercaptobenzothiazole, benzotriazole, and the like, or mixtures thereof. If one or more of the known inhibitors are employed together with the inhibitors of the present invention, the sum total of all inhibitors should be used in an "inhibitory effective amount", i.e., an amount sufficient to provide a measurable extent of corrosion inhibition with respect to the cooling system metal surfaces to be protected.

Other typical optional additives that may be employed include wetting agents and surfactants such as, for example, known ionic and non-ionic surfactants such as the poly(oxyalkylene) adducts of fatty alcohols; antifoams and/or lubricants such as the well-known polysiloxanes and the polyoxyalkylene glycols, as well as any other minor ingredients known in the antifreeze art.

Performance of the Antifreeze Concentrates

The antifreeze concentrates of the present invention are characterized by satisfactory stability against gelation prior to usage. Upon dilution to provide a working antifreeze, utilization of the antifreeze concentrates of this invention are characterized by exceptional resistance to gelation as well as freedom from undesirable precipitates. The relative amount of active monomeric silicate available should likewise be capable of being maximized. In other words, the improved stability resulting from the use of the present invention should provide the ability, particularly in its preferred embodiments, to substantially reduce, and perhaps even essentially eliminate, the formation of inactive, polymeric silica.

When optional corrosion inhibitors of an ionic nature are employed in the formulation, the present invention affords further advantages over conventional antifreezes. Thus, the inclusion of such optional inhibitors, particularly at the lower pH levels, tends to exacerbate the solubility and stability considerations of the system. The antifreeze composition of the present invention, imparting superior stability in the working antifreeze, provides a less sensitive and more efficient system. Indeed, the enhanced stability provided should allow greater latitude in formulation than has heretofore been possible.

The following Examples are merely illustrative of, and are not intended to limit, the present invention.

EXAMPLE 1

This Example illustrates the selectivity of various types of silanes in stabilizing silicate in an aqueous antifreeze (50 volume percent) under elevated test conditions.

In formulating each antifreeze concentrate, a standard base solution was prepared as follows:

| Base Fluid A* | |
|---|---|
| Component | Weight % |
| Ethylene Glycol | 93.5062 |
| Na$_2$B$_4$O$_7$.5H$_2$O | 3.7200 |
| NaOH, 50% aqueous | 1.4745 |
| Sodium Silicate, 40 clear** | 0.3663 |
| NaNO$_3$, 40% aqueous | 0.5000 |
| Sodium tolyltriazole | 0.2330 |
| Water | 0.2000 |
| Total Wt. Percent = | 100.0000 |

*Base fluid pH, 50 vol. % aqueous = 8.7 ASTM Reserve alkalinity (RA) = 56.6
**A liquid sodium silicate product of Diamond Shamrock Corporation having a solids content of 38.3 wt. % and manufactured for uses requiring high clarity.

Each silane as given in Table I below was added to Base Fluid A in an amount sufficient to provide 45.2 ppm of Si in the Base Fluid A concentrate. Before addition to Base Fluid A, each silane was presaponified with the number of moles of potassium hydroxide specified in Table I. The saponified silane esters specified were prepared as 25.8% by weight solutions of the silane ester with the specified moles of KOH with the balance added as a mixture of ⅓ ethylene glycol and ⅔ deionized water on a volume to volume basis. The saponification procedure utilized was as follows:

1. Into a suitable vessel was weighed the silane, ethylene glycol, and water.
2. The specified amount of KOH was added and, with the aid of a magnetic stirrer, was stirred until dissolved.
3. The resulting solution was poured into a glass bottle, the weight was recorded and the solution was lightly covered and placed in a 100° C. oven.
4. After a minimum of 16 hours at this temperature, the solution was made up to its original weight with water to replace evaporative loss and mixed well to provide the saponified silane.

In order to simulate in the laboratory the high test temperature conditions experienced by antifreeze in a car, a "boiling beaker test" was utilized. This test procedure involved placing 100 ml. of the antifreeze concentrate into a 300 ml. Pyrex beaker and adding 100 ml. of deionized water to the beaker. The beaker was then fitted with a watch cover glass and magnetic stirrer. The aqueous antifreeze in the beaker was then heated to boiling at 108° C. for one hour. The aqueous antifreeze was then cooled to room temperature; and the resulting precipitate was washed with deionized water, and dried to constant weight in an oven at 180° F. The weight of the dried precipitate is reported in Table I as milligrams of solids.

The test results are presented in Table I:

The results presented in Table I demonstrate the exceptional silicate stabilizing capacity of silane (D), which is in accordance with the present invention, in comparison to the other silanes tested, particularly as compared to commercial silanes (A) and (F).

This superior performance is readily apparent based upon the low precipitate weight of the formulation containing silane D, particularly as compared to the precipitate weight for structurally similar silanes B, C and E.

It is believed that the carbon chain length of silane D provides an optimized glycophilic (hydrophilic)/glycophobic (hydrophobic) balance for the silicone/silicate polymer in both the antifreeze concentrate and in the diluted aqueous antifreeze.

EXAMPLE 2

This Example illustrates the difference in silicate stabilization capacity of various silanes in an aluminum disc test with a cold finger. This Example presents a different, and less rigorous, test environment than that of the boiling beaker test set forth in Example 1.

A standard test method used in the antifreeze industry was employed to determine the inhibitory effect of the formulated antifreeze compositions using various silicones with respect to heat rejecting aluminum surfaces. This test method is described in *Corrosion*, 15,257t at 258t (1959) "Laboratory Methods for Determining Corrosion Rates Under Heat Flux Conditions", and also in an ASTM publication entitled, "Engine Coolant Testing: State of the Art," a symposium sponsored by ASTM Committee D-15, at pages 17-19 (Printed, May 1980), both incorporated herein by reference.

The following summarizes the test equipment and procedure used:

The apparatus consisted of a one liter flask, fitted with a condenser, a thermometer, a cold finger, a temperature controller, a 1½ inch diameter×¼ inch thick no. 319 aluminum casting alloy (herein the "aluminum disc"), and a soldering iron heat source.

The apparatus was charged with 900 ml. of the water-diluted antifreeze solution (1 volume/3 volume antifreeze/water) and heated to effect boiling at the aluminum disc surface and to maintain a solution temperature of about 80° C. Each water-diluted antifreeze test fluid was prepared by adding the silane to Base Fluid B, identified in Table II below:

TABLE II

| Ingredients | Base Fluid Composition (wt. % each ingredient) | | | | |
|---|---|---|---|---|---|
| | B | C | D | E | F |
| Ethylene Glycol | 93.5589 | 93.4062 | 93.3733 | 93.2578 | 93.4362 |
| Na$_2$B$_4$O$_7$.5H$_2$O | 3.8379 | 3.7200 | 3.7200 | 3.7200 | 3.7200 |
| NaOH, 50% Soln | 1.4640 | 1.4181 | 1.4181 | 1.4181 | 1.4181 |

TABLE I

| Silane # | Silane Structure | Saponified with # of moles of KOH | Weight of Precipitate (mg. of solids) |
|---|---|---|---|
| (A) | CH$_3$O(CH$_2$CH$_2$O)$_7$C$_3$H$_6$Si(OCH$_3$)$_3$ | 3 | 62 |
| (B) | NCC$_2$H$_4$Si(OC$_2$H$_5$)$_3$ | 4 | 78 |
| (C) | CH$_3$OOC(CH$_2$)$_6$Si(OCH$_3$)$_3$ | 4 | 62 |
| (D) | CH$_3$OOC(CH$_2$)$_{10}$Si(OCH$_3$)$_3$ | 4 | 4 |
| (E) | CH$_3$OOC(CH$_2$)$_{16}$Si(OCH$_3$)$_3$ | 4 | 139 |
| (F) | (CH$_3$)(O)(OCH$_3$)POC$_3$H$_6$Si(OCH$_3$)$_3$ | —* | 62 |
| Control - No Silane | | | 91 |

*a commercial 50 wt. percent aqueous saponified material sold under the trademark Q1-6083, a product of Dow Corning Corporation, and containing an organo-reactive anionic alkyl-phosphonate group and an inorganic sodium siliconate.

TABLE II-continued

| Ingredients | Base Fluid Composition (wt. % each ingredient) | | | | |
|---|---|---|---|---|---|
| | B | C | D | E | F |
| Nasil 50 clear | 0.3663 | 0.3663 | 0.3663 | 0.3663 | 0.3663 |
| NaOH, 50% Soln | 0.0564 | 0.0564 | 0.0564 | 0.0564 | 0.0564 |
| $H_2O$ | — | 0.2000 | 0.2000 | 0.2000 | 0.2000 |
| NaTTZ, 50% Soln | 0.1165 | 0.2330 | 0.2330 | 0.2330 | 0.2330 |
| $NaNO_3$, 50% Soln | 0.5000 | 0.5000 | 0.5000 | 0.5000 | 0.5000 |
| pH 33% | 8.88 | 8.88 | 8.87 | 8.88 | 8.86 |
| RA 10% | 51.60 | 51.78 | 51.08 | 51.00 | 50.16 |

The silane was added at a concentration of 0.1 wt. % based upon the total weight of Base Fluid B plus silane. If noted as saponified in Table III, the saponification procedure given in Example 1 was followed. The test duration was 168 hours. The weight loss of aluminum from the aluminum disc was determined and used as a measure of corrosion inhibitor effectiveness expressed as % inhibition.

The results are given in Table III:

TABLE III

| Test No. | Test Fluid** | AL Disc Test | |
|---|---|---|---|
| | | MG CFD* | MG AL Loss |
| 1 | Base Fluid B plus $CH_3O(CH_2CH_2O)_{7.2}C_3H_6Si(OCH_3)_3$ | 77 | 6 |
| 2 | Base Fluid B plus $(MeO)_3Si(CH_2)_{10}COOMe$ | 26 | 6 |
| 3 | Base Fluid B plus $(MeO)_3Si(CH_2)_{10}COOMe$ Sap.*** | 0 | 4 |
| 4 | Base Fluid B plus $(EtO)_3SiCH_2CH_2COOEt$ | 13 | 4 |
| 5 | Base Fluid B plus $(EtO)_3SiCH_2CH_2COOEt$ Sap.*** | 21 | 2 |
| 6 | Base Fluid B plus $(EtO)_3SiCH_2CH_2COOEt$ Sap.*** | 6 | 4 |
| 7 | Base Fluid B plus $(MeO)_3SiCH_2CH_2P(O)(OMe)_2$ | 57 | 6 |
| 8 | Base Fluid B plus $(MeO)_3SiCH_2CH_2P(O)(OMe)_2$ Sap.*** | 2 | 3 |
| 9 | Base Fluid B plus $(EtO)_3SiCH_2CH_2CN$ | 10 | 4 |
| 10 | Base Fluid B plus $(EtO)_3SiCH_2CH_2CN$ Sap.*** | 1 | 5 |
| 11 | Base Fluid B plus $(MeO)_3SiC_3H_6O\ CH_2CH(O)CH_2$ | 34 | 4 |
| 12 | Base Fluid B plus $(CH_3O(CH_2CH_2O)_{7.2}C_3H_6Si(OCH_3)_3$ Sap.*** | 93 | 2 |
| 13 | Base Fluid B plus $NCCH_2CH_2O(CH_2CH_2O)_{7.2}C_3H_6Si(OCH_3)_3$ Sap.** | 22 | 1 |

*Cold Finger Test
**Test Fluids contain 0.1% silane. "Et" denotes $C_2H_5$ and "Me" denotes $CH_3$.
****"Sap." denotes "saponified". The silanes were saponified with the following moles of KOH: in Test No. 3, two moles; Test No. 5, two moles; Test No. 6, 6.6 moles; Test No. 8, two moles; Test No. 10, one mole; Test No. 12, two moles; Test No. 13, two moles.

As can be seen from Table III, saponification to provide the organosilicon carboxylate results in improved performance relative to the unsaponified compounds utilized. Thus, while saponification at least in part occurs due to presence of water in the base fluid used, saponification prior to addition to the base fluid imparts enhanced stability as, for example, can be seen by comparing the performance of Test No. 2 (unsaponified) with Test No. 3 (saponified), the latter being in accordance with the present invention.

Additional aluminum disc tests were made using the base fluids identified in Table II. The silanes employed were incorporated into the formula at 45 ppm Si. The aluminum disc test results are shown in Table IV:

TABLE IV

| Test No. Al. | Base Fluid | Silane | MG-CFD | MG- |
|---|---|---|---|---|
| 15 | C | $CH_3O(CH_2CH_2O)_7C_3H_6Si(OCH_3)_3$ | 172 | 2 |
| 17 | D | $(EtO)_3SiCH_2CH_2CN$ Sap.*** | 20 | 1 |
| 18 | E | $(MeO)_3Si(CH_2)_{10}COOMe$ Sap.*** | 0.1 | 2 |
| 19 | F | $(CH_3)(O)(OCH_3)POC_3H_6Si(OCH_3)_3$ | 26 | 1 |

****"Sap." denotes "saponified". The silanes were saponified with the following moles of KOH: in Test No. 17, two moles of KOH; Test No. 18, two moles of KOH.

The results show the outstanding performance of the saponified $C_{10}$ carboxylate silane (Test No. 18), a preferred species of the present invention, with respect to minimizing silicate destabilization as measured by the low level of cold finger deposits of less than 0.1 mg. The cold finger deposits have been analyzed to be essentially all silica deposits.

We claim:

1. A method for protecting an internal combustion engine cooling system with an antifreeze concentrate diluted by addition of from about 25 to about 90 percent by weight water by introduction into an internal combustion engine cooling system wherein the antifreeze concentrate having a selected pH comprises:
   (a) an alcohol,
   (b) a buffer in an amount to maintain said pH for the antifreeze,
   (c) a silicate in a corrosion-inhibiting amount, and
   (d) an organosilicon carboxylate having the formula:

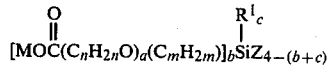

wherein a is from 0 to 20, b is 1 or 2, c is 0 or 1, n is an integer of 2 to 4, m is from 3 to 15, M is a monovalent metal cation, $R^1$ is selected from the group consisting of hydrogen, monovalent hydrocarbon radicals and substituted monovalent hydrocarbon radicals, and Z is a hydrolyzable moiety attached to silicon, with the proviso that when a is 0, m is from about 7 to about 15, said carboxylate being present in an amount sufficient to stabilize the silicate.

2. The method of claim 1 wherein a is 0, b is 1, and c is 0.

3. The method of claim 2 wherein m is 10.

4. The method of claim 1 wherein a is from about 5 to 13, b is 1, c is 0, m is 3 and n is 2.

5. The method of claim 1 wherein component (c) is an inorganic silicate described as a distribution of species represented by units having the empirical formula:

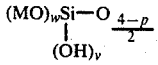

wherein M is a monovalent cation that forms a glycol soluble silicate selected from the group consisting of sodium, potassium, lithium, rubidium and tetraorganoammonium cations, w has a value of from 1 to 4 inclusive, v has a value from 0 to 3 inclusive and p has a value from 1 to 4 inclusive which is equal to the sum of w and v.

6. The method of claim 1 wherein component (c) is an organic silicate ester having the formula:

$$Si(OR)_4$$

wherein R is selected from the group consisting of alkyl, aryl, alkoxyalkyl, alkoxyaryl and mixtures thereof.

7. The method of any of claims 1 through 6 made from an antifreeze concentrate wherein the amount of component (c) is between 100 and 1000 ppm of equivalent Si based on the total weight of the antifreeze concentrate.

8. The method of any of claims 1 through 6 made from a concentrate wherein the amount of component (d) is between about 10 and about 100 ppm of silicon equivalents based on the weight of the antifreeze concentrate.

9. The method of any of claims 1 through 6 wherein said pH is between about 8 and about 11.

10. The method of any of claims 1 through 6 wherein said pH is between about 9 and about 10.5.

11. The method of any of claims 1 through 6 wherein said pH is between about 8 and about 10.5.

12. The method of any of claims 1 through 6 which additionally contains carbonate or bicarbonate, or a mixture thereof.

13. The method of any of claims 1 through 6 made from a concentrate wherein the amount of component (b) is between about 1 and about 5 wt. % based on the weight of the concentrate.

14. A method for protecting an internal combustion engine cooling system with an antifreeze concentrate diluted by addition of from about 25 to about 90 percent by weight water by introduction into an internal combustion engine cooling system wherein the antifreeze concentrate having a selected pH comprises a composition made from the following components:
(a) an alcohol,
(b) a buffer in an amount to maintain said pH for the antifreeze,
(c) a silicate in a corrosion-inhibiting amount, and
(d) an organosilicon carboxylate percursor having the formula:

$$[Y-(C_nH_{2n}O)_a(C_mH_{2m})]_b SiZ_{4-(b+c)}^{R^{1c}}$$

wherein Y is a hydrolyzable moiety selected from the group consisting of

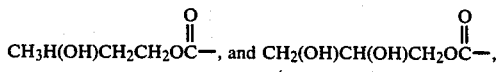

a is from 0 to 20, b is 1 or 2, c is 0 or 1, n is an integer of from 2 to 4, m is from 3 to 15, M is a monovalent metal cation, $R^1$ is selected from the group consisting of hydrogen, monovalent hydrocarbon radicals and substituted monovalent hydrocarbon radicals, and Z is a hydrolyzable moiety attached to silicon, with the proviso that when a is 0, m is from about 7 to about 15, said organosilicon carboxylate precursor being added in an amount sufficient to stabilize the silicate in said antifreeze.

15. The method of claim 14 wherein Y is $$\overset{O}{\underset{\|}{MOC}}- \text{ and } \overset{O}{\underset{\|}{HOCH_2CH_2OC}}-,$$

and Z is $-OCH_2CH_2OH$.

16. A method according to claim 1 or claim 14 wherein Z is at least one of acyloxy containing species, alkyloxy containing species, aryloxy containing species, aralkyloxy containing species, alkaryloxy containing species, alkyleneoxy containing species, hydroxy alkyloxy containing species, hydroxy polyalkyleneoxy alkyloxy containing species, alkoxy polyalkyleneoxy alkyloxy containing species, acyloxy polyalkyleneoxy alkyloxy containing species, alkoxy alkyloxy containing species, acyloxy alkyloxy containing species, cyano alkyloxy containing species, cyano polyalkyleneoxy alkyloxy containing species, amino alkyloxy containing species, amino alkyloxy containing species, dialkylamino alkyloxy containing species, alkanolamino alkyloxy containing species, dialkanolamino alkyloxy containing species, carboxy alkyloxy containing species, carboxy polyalkyleneoxy alkyloxy containing species, carboalkoxy containing species and carboalkoxy alkyloxy containing species.

17. A method according to claim 1 or claim 14 wherein M in the organosilicone carboxylate is a monovalent metal cation.

18. A method according to claim 17 wherein said monovalent cation is at least one of sodium or potassium.

19. A method for protecting an internal combustion engine cooling system with an antifreeze concentrate diluted by addition of from about 25 to about 90 percent by weight water by introduction into an internal combustion engine cooling system wherein the antifreeze concentrate having a selected pH comprises:
(a) an alcohol selected from the group consisting of ethanol, propanol, butanol, ethylene glycol, diethylene glycol, propylene glycol, glycerol, butylene glycol and mixtures thereof;
(b) a buffer in an amount to maintain said pH for the antifreeze;
(c) a silicate in a corrosion-inhibiting amount; and
(d) an organosilicon carboxylate having the formula:

$$[\overset{O}{\underset{\|}{MOC}}(C_nH_{2n}O)_a(C_mH_{2m})]_b \overset{R^1_c}{\underset{|}{Si}} Z_{4-(b+c)}$$

wherein a is 0, b is 1, c is 0 or 1, n is an integer of 2 to 4, m is 10, M is a monovalent metal cation, $R^1$ is selected from the group consisting of hydrogen, monovalent hydrocarbon radicals and substituted monovalent hydrocarbon radicals, and Z is a hydrolyzable moiety attached to silicon, wherein said carboxylate is present in an amount sufficient to stabilize the corrosion-inhibiting amount of silicate.

20. A method according to claim 19 wherein component (c) is an inorganic silicate described as a distribution of species represented by units having the empirical formula:

$$(MO)_w\underset{\underset{(OH)_v}{|}}{Si}{-}O_{\frac{4-p}{2}}$$

wherein M is a monovalent cation that forms a glycol soluble silicate selected from the group consisting of sodium, potassium, lithium rubidium and tetraorganoammonium cations, w has a value of from 1 to 4 inclusive, v has a value from 0 to 3 inclusive and p has a value from 1 to 4 inclusive which is equal to the sum of w and v.

21. A method according to claim 19 wherein component (c) is an organic silicate ester having the formula:

$$Si(OR)_4$$

wherein R is selected from the group consisting of alkyl, aryl, alkoxyalkyl, alkoxyaryl and mixtures thereof.

22. A method according to claims 19 or 20 or 21 having an antifreeze concentrate wherein the amount of component (c) is between 100 and 1000 ppm of equivalent Si based on the total weight of the antifreeze concentrate.

23. A method according to claims 19 or 20 or 21 made from a concentrate wherein the amount of component (d) is between 10 and about 100 ppm of silicon equivalents based on the weight of the antifreeze concentrate.

24. A method according to claims 19 or 20 or 21 wherein said pH is between about 8 and about 11.

25. A method according to claims 19 or 20 wherein said pH is between about 9 and about 10.5.

26. A method according to claim 21 wherein said pH is between about 9 and about 10.5.

27. A method according to claims 19 or 20 or 21 which additionally contains carbonate or bicarbonate, or a mixture thereof.

28. A method according to claims 19 or 20 or 21 made having an antifreeze concentrate wherein the amount of component (b) is between about 1 and about 5 wt. percent based on the weight of the antifreeze concentrate.

29. A method for protecting an internal combustion engine cooling system with an antifreeze concentrate diluted by addition of from about 25 to about 90 percent by weight water by introduction into an internal combustion engine cooling system wherein the antifreeze concentrate having a selected pH comprises:
(a) an alcohol selected from the group consisting of ethanol, propanol, butanol, ethylene glycol, diethylene glycol, propylene glycol, glycerol, butylene glycol and mixtures thereof;
(b) a buffer in an amount to maintain said pH for the antifreeze;
(c) a silicate in a corrosion-inhibiting amount; and
(d) an organosilicon carboxylate having the formula:

$$[\overset{O}{\overset{\|}{M O C}}(C_nH_{2n}O)_a(C_mH_{2m})]_b\overset{R^1_c}{\overset{|}{Si}}Z_{4-(b+c)}$$

wherein a is from 0, b is 1, c is 0 or 1, n is an integer of 2 to 4, m is 10, M is a monovalent metal cation, $R^1$ is selected from the group consisting of hydrogen, monovalent hydrocarbon radicals and substituted monovalent hydrocarbon radicals, and Z is a hydrolyzable moiety attached to silicon, with the proviso that when a is 0, m is from about 7 to about 15, said organosilicon carboxylate precursor being added in an amount sufficient to stabilize the silicate in said antifreeze.

30. A method according to claim 29 wherein Y is $$\overset{O}{\overset{\|}{M O C}}{-} \text{ or } HOCH_2CH_2O\overset{O}{\overset{\|}{C}}{-},$$

and Z is $-OCH_2CH_2OH$.

31. A method according to claim 1 or claim 19 wherein a precipitate of 60 milligrams or less is formed when evaluated by the boiling beaker test.

32. A method according to claim 31 wherein a precipitate of less than about 10 mg. precipitate is formed.

33. A method according to claim 1 or claim 19 wherein said antifreeze concentrate is prepared by saponification of the organosilicon carboxylate prior to admixture with components (a), (b) and (c).

34. A method for protecting an internal combustion engine cooling system with an antifreeze concentrate diluted by addition of from about 25 to about 90 percent by weight water by introduction into an internal combustion engine cooling system wherein the antifreeze concentrate having a selected pH comprises:
(a) an alcohol selected from the group consisting of ethanol, propanol, butanol, ethylene glycol, diethylene glycol, propylene glycol, glycerol, butylene glycol and mixtures thereof;
(b) a buffer in an amount to maintain said pH for the antifreeze;
(c) a silicate in a corrosion-inhibiting amount; and
(d) an organosilicon carboxylate having the formula:

$$[\overset{O}{\overset{\|}{M O C}}(C_nH_{2n}O)_a(C_mH_{2m})]_b\overset{R^1_c}{\overset{|}{Si}}Z_{4-(b+c)}$$

wherein a is from 5 to about 15, b is 1, c is 0 or 1, n is an integer of 2 to 4, m is 10, M is a monovalent metal cation, $R^1$ is selected from the group consisting of hydrogen, monovalent hydrocarbon radicals and substituted monovalent hydrocarbon radicals, and Z is a hydrolyzable moiety attached to silicon, wherein said carboxylate is present in an amount sufficient to stabilize the corrosion-inhibiting amount of silicate.

35. A method according to claim 34 wherein component (c) is an inorganic silicate described as a distribution of species represented by units having the empirical formula:

$$(MO)_w\underset{\underset{(OH)_v}{|}}{Si}{-}O_{\frac{4-p}{2}}$$

wherein M is a monovalent cation that forms a glycol soluble silicate selected from the group consisting of sodium, potassium, lithium, rubidium and tetraorganoammonium cations, w has a value of from 1 to 4 inclusive, v has a value from 0 to 3 inclusive and p has a value from 1 to 4 inclusive which is equal to the sum of w and v.

36. A method according to claim 34 wherein component (c) is an organic silicate ester having the formula:

$$Si(OR)_4$$

wherein R is selected from the group consisting of alkyl, aryl, alkoxyalkyl, alkoxyaryl and mixtures thereof.

37. A method according to claim 34 made from an antifreeze concentrate wherein the amount of component (c) is between 100 and 1000 ppm of equivalent Si based on the total weight of the antifreeze concentrate.

38. A method according to claim 34 made from a concentrate wherein the amount of component (d) is between 10 and about 100 ppm of silicon equivalents based on the weight of the antifreeze concentrate.

39. A method according to claim 34 wherein said pH is between about 8 and about 11.

40. A method according to claim 34 which additionally contains carbonate or bicarbonate, or a mixture thereof.

41. A method according to claim 34 made from a concentrate wherein the amount of component (b) is between about 1 and about 5 wt. percent based on the weight of the concentrate.

42. A method according to claim 1 wherein the antifreeze concentrate having a selected pH is prepared by mixing the following components:

(a) an alcohol selected from the group consisting of ethylene glycol, diethylene glycol and mixtures thereof;

(b) a buffer in an amount to maintain said pH for the antifreeze;

(c) a silicate in a corrosion-inhibiting amount; and (d) an organosilicon carboxylate percursor having the formula:

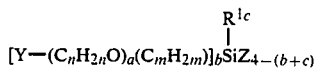

wherein Y is a hydrolyzable moiety selected from the group consisting of

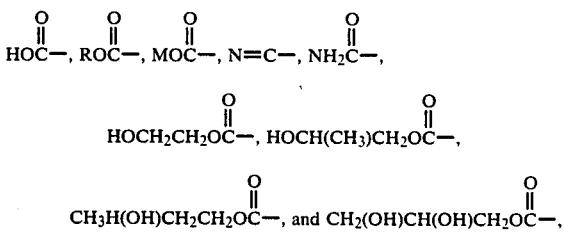

a is from 0 to 20, b is 1 or 2, c is 0 or 1, n is an integer of from 2 to 4, m is 10, M is a monovalent metal cation, $R^1$ is selected from the group consisting of hydrogen, monovalent hydrocarbon radicals and substituted monovalent hydrocarbon radicals, and Z is a hydrolysable moiety attached to silicon, with the proviso that when a is 0, m is from about 7 to about 15, said organosilicon carboxylate precursor being added in an amount sufficient to stabilize the silicate in said antifreeze and wherein the organosilicon carboxylate precursor is saponified prior to admixture with components (a), (b) and (c).

43. A method according to claim 42 wherein Y is

and Z is $-OCH_2CH_2OH$.

* * * * *